US006274349B1

(12) United States Patent
Eyal et al.

(10) Patent No.: US 6,274,349 B1
(45) Date of Patent: Aug. 14, 2001

(54) PROCESS FOR THE PREPARATION OF LONG-CHAIN ALKYLGLYCOSIDES

(75) Inventors: Aharon Meir Eyal; Asher Vitner; Tal Reuveni, all of Jerusalem (IL)

(73) Assignee: Yissum Research Development Company of the Hebrew University of Jerusalem (IL)

( * ) Notice: Subject to any disclaimer, the term of this patent is extended or adjusted under 35 U.S.C. 154(b) by 0 days.

(21) Appl. No.: 09/319,522

(22) PCT Filed: Jan. 6, 1998

(86) PCT No.: PCT/US98/00052

§ 371 Date: Aug. 23, 1999

§ 102(e) Date: Aug. 23, 1999

(87) PCT Pub. No.: WO98/30714

PCT Pub. Date: Jul. 16, 1998

(30) Foreign Application Priority Data

Jan. 9, 1997 (IL) ........................................................ 119985

(51) Int. Cl.$^7$ ...................................................... C12P 19/44
(52) U.S. Cl. ................................. 435/74; 435/72; 536/4.1; 536/18.6
(58) Field of Search ...................... 435/74, 72; 536/4.1, 536/18.6

(56) References Cited

U.S. PATENT DOCUMENTS 6,037,151 * 3/2000 Eyal et al. ............................. 435/74

FOREIGN PATENT DOCUMENTS

WO96/11281    4/1996  (WO) .

OTHER PUBLICATIONS

Trincone et al, Biotech. Letters, 13(4):235–240 1991.*
Database Internet http://www.biocat.com/facts/press/press.96/press.html; DIVERSA press release; 14.02.1996 XP002064573.
Vulfson, "Enzymatic Synthesis of Surfactants," *Surfactants Lipid Chem.*, pp. 16–37 (1992).
Sarney et al., "Application of Enzymes to the Synthesis of Surfactants," *Trends in Biotechnology* 13:164–172 (1995).
Kengen et al., "Purification and Characterization of an Extremely Thermostable β–Glucosidase from the Hyperthermophilic Archaeon *Pyrococcus Furiosus*," *European Journal of Biochemistry* 213:305–312 (1993).

Voorhorst et al., "Characterization of the *celB* Gene Coding for β–Glucosidase from the Hyperthermophilic Archaeon *Pyrococcus Furiosus* and Its Expression and Site–Directed Mutation in *Escherichia coli*," *Journal of Bacteriology* 177:7105–7111 (1995).
Ladrat et al., "A New Thermostable Glucose–Activated β–Glucosidase from the Hyperthermophilic Marine Archaebacterium *Pyrococcus Abyssi*: Purification and Characterization," *Journal of Marine Biotechnology* 4:192–199 (1996).
Ladrat et al., "Mise en évidence d'enzymes thermostables chez des micro–organismes thermophiles d'origine hydrothermale," *C.R. Acad. Sci. Paris, Sciences De La Vie* 318:423–429 (1995).
Li et al., "Chemical and Enzymatic Synthesis of Glycoconjugates 2. High Yielding Regioselective Synthesis of N–Acetyllactosamine by Use of Recombinant Thermophilic Glycosidases Library," *Tetrahedron Letters* 38 :7967–7970 (1997).
Chahid et al., "Biocatalyzed Octylglycoside Synthesis from a Disaccharide," *Biotechnology Letters* 16:795–800 (1994).
Vulfson et al., "Alkyl–β–Glucoside Synthesis in a Water–Organic Two–Phase System," *Biotechnology Letters* 12:397–402 (1990).
Vulfson et al., "Glycosidases in Organic Solvents: I. Alkyl–β–Glucoside Synthesis in a Water–Organic Two–Phase System," *Enzyme Microb. Technol.* 12:950–954 (1990).
Drouet et al., "Enzymatic Synthesis of Alkyl β–D–Xylosides by Transxylosylation and Reverse Hydrolysis," *Biotechnology and Bioengineering* 43:1075–1080 (1994).
Ljunger et al., "Enzymatic Synthesis of Octyl–β–Glucoside in Octanol at Controlled Water Activity," *Enzyme Microb. Technol.* 16:751–755 (1994).

* cited by examiner

Primary Examiner—Francisco Prats
(74) Attorney, Agent, or Firm—Williams, Morgan & Amerson, P.C.

(57) ABSTRACT

The invention provides a process for the preparation of long-chain alkyl glycosides, comprising reacting at least one substrate selected from a group consisting a carbohydrates and carbohydrates sources and at least one fatty alkanol of at least eight carbon atoms in a medium consisting of at least one glycosidase enzyme having a temperature optimum greater than 60° C. and having thermal stability half-life of greater than 24 hours at 80° C.

21 Claims, No Drawings

PROCESS FOR THE PREPARATION OF LONG-CHAIN ALKYLGLYCOSIDES

The present invention relates to a process for the preparation of long-chain alkyl glycosides.

More particularly, the present invention relates to an enzymatic process for the preparation of long-chain alkyl glycosides.

As described, e.g., as background in U.S. Pat. No. 5,191,071, which is directed to monoesters of glycosides, surface active compounds constitute an exceedingly important class of industrial organic chemicals finding a wide variety of uses, e.g., as detergents for washing purposes, as emulsifiers in food and feed products, or even as functional ingredients in many personal care products, such as shampoos, moisturizing creams, etc.

Basically, on the molecular level, surfactants are characterised by and owe their properties to the presence of hydrophobic and hydrophilic regions within the individual surfactant molecules. This particular constellation can be established in numerous fashions, e.g., by combining sulphonic acid residue, a quartenised ammonium entity or a glycerol moiety with an alkyl chain, as is the case in the linear alkyl sulfonates, the quarternised alkyl amines, and the monoglycosides, respectively. In the actual design of such surfactant molecules, major consideration is given to the detailed molecular architecture of the compounds, important issues being the precise balance between the hydrophilic and hydrophobic domains of the surfactant molecules and the actual special arrangements of these parts of the molecules. Besides, consideration is obviously given to the possibilities of actually producing the surfactants in high yielding processes and on the basis of raw materials available at reasonable costs. The environmental issues related to the eventual loading of the surfactant into the environment are finally a matter of major concern.

Due to the above considerations, over the years there has been a keen interest in preparing surfactant molecules on the basis of sugars and fatty acids or fatty alcohols, e.g., as sugar esters or ethers. Such conjugates were expected to exhibit surface active properties due to the presence of the hydrophilic sugar regions and the hydrophobic fatty acid or fatty alcohol residues. The balance, and thus the precise properties of the conjugates, might be varied through changes of the nature of the sugar and the fatty acid or fatty alcohol residues; the materials would be produceable from exceedingly cheap raw materials; and the surfactants, being composed of, and degradable into, natural constituents, would not be harmful to the environment.

As described and discussed by D. Balzer in *Tenside Surf. Det.*, Vol. 28, p. 6 (1991), alkyl polyglycosides were described for the first time about 100 years ago. However, it was not until 1934 that their potential as surface active substances was appreciated in a patent to H. Th. Boehme AG of Chemnitz. They then fell into obscurity for a long time, probably because not only were they difficult to manufacture, especially as regards the control of the colour quality, but also because of the many surfactants already in production. It was not until about 10 years ago that this old class of surfactants was unearthed again, against a background of increasing environmental concerns, but also because of the spectre of a raw material, i.e., crude oil, shortage.

Alkyl polyglycosides are non-ionic surfactants prepared on the basis of renewable raw materials, namely, starch and fat, or their derivatives glucose and fatty alcohols. By utilising D-glucose, probably the most common natural organic monomer unit, as a surfactant base, the range of raw materials for surfactants is advantageously expanded. This statement is underlined by the excellent application properties and favourable eco-tox data of the alkyl polyglycosides.

Thus, in recent years, several companies have begun to market alkyl polyglycoside surfactants.

In the 1980's, it was reported that Horizon Chemical, a newly-formed division of A. E. Staley Manufacturing Co., was commercializing a new generation of alkyl polyglycoside surfactants, superior in quality to surfactants offered, and suitable for use in a wide range of surfactant applications, including household laundry, dishwashing and general purpose cleaners.

The alkyl polyglycosides were described as being non-ionic in nature, but with properties much different from ethoxylated fatty alcohols or alkyl phenols.

As described in said press release, the alkyl polyglycoside surfactants can be used as primary surfactants, or in combination with other surfactants. Synergistic performance has been observed when alkyl polyglycosides are combined with both linear alkylbenzene sulfonate (LAS) and linear alcohol ethoxylate (LAE).

These surfactants are more soluble than other surfactants and are stable under a wide range of conditions. They are milder to the skin than LAS and LAE, and are non-toxic and readily biodegradable. Their foam characteristics in combination with anionic surfactants, combined with their mildness and solubility allows for, the formulation of a mild, high performance hand dishwashing product with non-ionic grease-cutting ability, but requiring less hydrotrope and no foam booster.

The solubility of the alkyl polyglycoside surfactants in concentrated electrolyte solutions allows the formulation of a stable, concentrated surfactant solution, containing 20–30% of a conventional inorganic builder. In addition, the solubility and solvent properties of these surfactants allow the formulation of a hard surface cleaner which requires no rinsing and less solvent than current products. The solubility, self-hydrotroping and electrolyte compatibility of alkyl polyglycoside surfactants enable slurry concentrations to be increased, thereby allowing processing rates to be raised and cost to be reduced.

The development of copious amounts of stable foam is a primary criteria for a premium dishwashing liquid. Other important factors include mildness and grease emulsification. Alkyl polyglycoside surfactants, unlike ethoxylated fatty alcohols, bring non-ionic grease-cutting strength and mildness to hand dishwashing. These properties make them an ideal surfactant for this end use.

In a press release issued Jan. 5, 1993, it is reported that Henkel Cospha Dusseldorf launched what it describes as a new generation of surfactants, specially developed for the cosmetics industry and sold under the product name Plantaren. Plantaren is an alkyl polyglycoside from renewable raw materials: glucose derived from corn, and fatty alcohols from coconut and palm kernel oils. It is also biodegradable under aerobic and anaerobic conditions. These non-ionic surfactants are said to provide a broad spectrum of possibilities for formulation in the cosmetics sector. Plantaren surfactants are described as being suitable for a variety of personal care applications, such as shampoos, hair conditioners, facial cleansers and bath products, and are found to have very good foaming and cleaning performance, with extraordinary mildness to skin and eyes.

It will thus be realized that alkyl glycosides are now becoming major surfactants of interest and use.

Several patents have issued which propose various processes for the production of alkyl glycosides, e.g., European Patents 0096917 and 0132043 and U.S. Pat. Nos. 3,839,318; 4,393,203; 5,206,357 and 5,212,292. All of the processes described in said patents, however, are carried out by reacting a carbohydrate and an alkanol in the presence of an acidic catalys and at a temperature range of about 80–150° C. and mostly in a preferred range above 100° C., which presents serious drawbacks in that, at said temperatures, there is both undesirable isomerization and caramelization of sugars, resulting in discoloration and a consequent need for complicated and/or expensive purification steps.

Thus, it will be realized that at the relatively high temperatures and in the presence of an acidic catalyst, many undesirable reactions take place, resulting in difficulties in controlling production in terms of the isomer formed and in the number of glucose groups in the product molecule, forming by-products of lower biodegradability and, what seems to be even more problematic, adding coloring compounds to produce a dark-colored product. Many attempts have been made to reduce the decoloration, e.g., through the gradual addition of the sugar at a rate that limits the amount of unreacted sugar in the reaction mixture to less than 10% by weight [see, e.g., EP 0096917]. Other suggested routes include selecting a better catalyst [U.S. Pat. No. 5,206,357 and EP 0132043] and lowering the acidity and the temperature. Alternatively, processes were proposed for removing the color from the product through treatment with various reducing agents. Thus, e.g., U.S. Pat. No. 4,762,918 teaches a process for reducing the color of a glycoside composition including contacting the glycoside composition under hydrogenation conditions with a hydrogenation catalyst in the presence of hydrogen.

Similarly, U.S. Pat. No. 5,104,981, issued in 1992 and filed in 1989, also states, in column 1, lines 23–26, that "the most serious problem in the production of alkyl glycosides is that various procedures during the production process thereof frequently cause deterioration of the hue of the product." Said patent, after discussing the problems in other prior art patents, teaches that "these materials causing coloration may be readily reduced by contacting the alkyl glycoside reaction product containing these materials with a specific metal/hydrogen complex."

In view of the difficulties encountered in production of these compounds by chemical means and their attractiveness as industrial surfactants, much attention has been devoted during recent years to the possibility of utilising enzymes for synthesis thereof. One major rationale behind this interest is that enzymes are known to exhibit a high degree of regio- and enantioselectivity, which might be exploited for selective etherification of a hydroxy group in a sugar molecule, and which are used effectively at conditions of mild temperature and mild pH. Two articles describing this approach have been published in 1992. The first is an article by Z. Chahid, et al., entitled, "Effect of Water Activity on Enzymatic Synthesis of Alkyl Glycosides," *Biotechnology Letters*, Vol. 14, No. 4, pp. 281–284 (April 1992). The second is an article by V. Laroute, et al., entitled "Glycoside Synthesis by Glucoamylase or b-Glycosidase in Organic Solvents," *Biotechnology Letters*, Vol. 14, No. 3, pp. 169–174 (March 1992).

Both the above-mentioned articles describe biocatalysed alkyl glycoside synthesis in the presence of a b-glycosidase and both teach that the synthesis is effected by the carbon chain length of the alcohol used, the first article stating that "for both enzymes an augmentation of carbon chain length involves a decrease of synthesis yields," and the second article even more unequivocally stating that:

"Experiments carried out under the same conditions with C12 lauric alcohol led to virtually nil yield, which confirms the previous hypothesis. Moreover, if the line in FIG. 2 is extrapolated, it can be seen that beyond a chain length of 9 to 10 carbons, the synthesis reaction should not be possible under our experimental conditions."

Similarly, FR-A-2680373 discloses a method of preparing alkyl glycosides from maltose and other starch hydrolysis products using α-glycosidases. However, it is specifically stated that the presences of β-glycosidase prevented the stereospecific synthesis of α-glycosides. In Agic. Biol. Chem. 52 (9), 2375–2377, 1998, the effect of β-glycosidase on the formulation of various glycosides is demonstrated. Good activity is shown for low carbon number water-miscible primary alcohols, but not for water-insoluble alcohols.

With the above state of the art in mind, it has now been surprisingly found that, contrary to the teachings in said articles, an enzyme-catalysed direct reaction between one substrate selected from a group consisting of carbohydrates and carbohydrate sources and at least one fatty alkanol of at least eight carbon atoms is indeed possible.

It has been discovered that certain thermal stable glycosidase enzymes greatly enhance the enzymatic formation of long-chain alkyl glycosides. One source of thermal stable glycosidases are those prepared by cloning of genetic material from hyperthermophilic bacteria. One commercial source of such enzymes is Recombinant BioCatalysis Inc. (RBI), 512 Elmwood Court, Sharon, Pa. 19079, U.S.A.

Thus according to the present invention, there is now provided a process for the preparation of long-chain alkyl glycosides, comprising reacting at least one substrate selected from a group consisting of carbohydrates and carbohydrate sources and at least one fatty alkanol of at least eight carbon atoms in a medium consisting of at least one glycosidase enzyme having a temperature optimum greater than 60° C. and having thermal stability half-life of greater than 24 hours at 80° C.

In preferred embodiments of the present invention said enzyme is characterised by the ability of 0.05 mg of said enzyme to catalyze a reaction between 750 mg dodecanol and 50 mg of beta methyl glycoside at 80° C. to achieve a rate of dodecyl glycoside formation of at least 20 micromole per day per mg of the enzyme.

In particularly preferred embodiments of the present invention, said enzyme is characterised by the ability of 0.05 mg of said enzyme to catalyze a reaction between 750 mg dodecanol and 50 mg of beta methyl glycoside at 80° C. to achieve a rate of dodecyl glycoside formation of at least 50 micromole per day per mg of the enzyme.

In especially preferred embodiments of the present invention said enzyme is characterised by the ability of 0.05 mg of said enzyme to catalyze a reaction between 750 mg dodecanol and 50 mg of beta methyl glycoside at 80° C. to achieve a rate of dodecyl glycoside formation of at least 100 micromole per day per mg of the enzyme.

Thus as indicated, the enzymes for use in the present invention are preferably selected from the CloneZyme Glycosidase Library of Recombinant BioCatalysis Inc (RBI), said enzyme being characterised by the ability of 0.05 mg of said enzyme to catalyze a reaction between 750 mg dodecanol and 50 mg of beta methyl glycoside at 80° C. to achieve a rate of dodecyl glycoside formation of at least 20 micromole per day per mg of the enzyme.

Recombinant BioCatalysis Inc (RBI) has libraries of recombinant enzymes called CloneZymes. Its Glycosidase CloneZyme library contains ten unique thermostable glycosidases supplied in partially purified form. Glycosidases hydrolyse the glycosidic linkages in polymers of furanose and pyranose sugars. These enzymes are very specific for the glycosyl portion of the substrate as well as for the position and stereochemistry of the glycosidic bond. In addition to their utility in the rections requiring hydrolysis of saccharides, glycosidases also used in sugar modification and stereospecific oligo and polysaccharides synthesis. Glycosidases also transfer glycosyl residues to primary secondary and tertiary alcohols to form glycoconjugate.

Recombinant BioCatalysis Inc. tested the specific activity of the ten members of the Glycosiadse CloneZyme library in hydrolysis of p-nitro alpha or beta glycoside at 90°. One unit of specific activity is defined as the amount of enzyme that catalyzes the formation of one micromole of p-nitrophenolate per minute per mg protein at 90° C. The specific activities reported for the various enzymes were: Gly001-01=46.1, Gly001-02=3121, Gly001-03=250, Gly001-04=52, Gly001-05=0.9, Gly001-06=45.1, Gly001-07=4.2, Gly001-08=666, Gly001-09=131 and Gly001-10= 19.6.

RBI explains that the assays are specific for the hydrolysis of the selected sugar. The activity is dependent on the nature of the reaction (hydrolysis vs. condensation (i.e. reverse hydrolysis) or transglucosidation) on the R group (the moiety bound to the sugar or to be bound to it) and on the reaction conditions such as temperature, pH and solvent: "The customer may find the enzymes; chemo-, regio- and stereospecificity to include other glycosides or R-groups not tested. Regarding reverse hydrolysis or transglucosidation under user-defined substrate, solvent and rection conditions, the enzymes may also display unique and useful characteristics. Each Clonezyme library member should be screened by the user for identification of the optimum candidate enzyme for the desired use."

No testing of long-chain alkylglycoside hydrolysis or formation is reported by RBI.

The thermal stability half life at a particular temperature is defined as the time in which the activity of an enzyme at this temperature drops to one half of the initial one. For enzymes suitable for the present invention, this half life is greater than 24 hours at 80° C., meaning that at 80° C. the activity of the enzyme after 24 hours is greater than one half of the initial activity.

RBI determined the temperature stability of its Glycosidase CloneZyme library enzymes in the hydrolysis of p-nitro alpha or beta glycoside:

Gly001-01—50% activity remaining after 9 hours at 80° C.;

Gly001-02—92% activity remaining after 145 hours at 90° C.;

Gly001-03—95% activity remaining after 130 hours at 80° C.;

Gly001-04—66% activity remaining after 130 hours at 80° C.;

Gly001-05—50% activity remaining after 78 hours at 80° C.;

Gly001-06—75% activity remaining after 130 hours at 80° C.;

Gly001-07—55% activity remaining after 130 hours at 80° C.;

Gly001-08—50% activity remaining after 40 hours at 80° C.;

Gly001-09—98% activity remaining after 130 hours at 80° C.; and,

Gly001-10—50% activity remaining after 8 hours at 80° C.

Based on this data, and assuming that the temperature stability in the reaction for the preparation of long-chain alkyl glycoside is similar to that of hydrolysis of p-nitro alpha or beta glycoside, Gly001-02, -03, -04, -05, -06, -07, -08 and -9 are suitable for the present invention.

The thermal stable enzymes allow for the production of alkyl glycosides at much higher temperatures and higher yields than prior art enzymes. It is preferred that the reaction temperature of the process described herein be run at a temperature higher than 50° C., preferably higher than 70° C. and most preferably higher than 80° C.

Preferably, said glucose-containing reactant is obtained from starch hydrolysis and said carbohydrates are selected from a group consisting of mono-, di- and tri-sugars.

More specifically, said carbohydrate sources are preferably selected from a group consisting of glycosides made of mono-, di- and tri-sugars and C1 to C4 alkanols.

In U.S. Pat. No. 3,598,865 there is disclosed a preparation of long chain alkyl glycosides by reacting monosaccharides, or compounds hydrolyzable to monosaccharides, with $C_8$–$C_{25}$ monohydric alcohols, in the presence of acid catalysts and latent solvents. Thus, said patent discloses a process for the production of glycosides in the classical reaction using an organic or an inorganic acid as a catalyst and therefore it is not relevant to the enzymatic reactions of the present invention.

In U.S. Pat. No. 4,859,589 there is disclosed an enzymatic method for preparing epoxy-containing carbohydrates. More specifically, said patent discloses a method for preparing an epoxy substituted sugar in an enzymatic reaction. Said patent, however, neither teaches nor discloses the use of thermal stable enzymes as taught in the present invention.

In PCT/GB95/02373 there is described and claimed a process for the preparation of long-chain alkyl glycosides comprising reacting a glycose-containing reactant with a long-chain fatty alcohol in the presence of a glycosidase and a reaction promoter characterised in that a $C_8$–$C_{18}$ fatty alcohol is reacted in the presence of a β-glycoside and in that the promoter is selected from the group consisting of formamide, methyl formamide, dimethyl formamide, a $C_1$–$C_4$ alcohol, sodium dodecal sulfonate (SDS), a long-chain alkyl glycoside, dioxane, acetone, dimethylsulfoxide, and sulfobutanedioic acid, 1,4-bis (2-ehtylhexyl) ester sodium salt and mixtures thereof, as well as solvents having a polar component of solubility parameter in the range of 5–13, and a hydrogen bonding component of solubility parameter in the range of 4–11 and said promoter is present in an amount of less than 50 wt % of the total reaction mixture.

In contradistinction to the teachings and limitation of said process it has now been surprisingly found that the enzymes utilized in the present process result in reaction rates several magnitudes greater than those achieved with the thermally stable β-glycosidase enzymes suggested and exemplified in said earlier co-pending specification as can be seen from example 1 hereinafter.

Thus in especially preferred embodiments of the present invention said enzyme is selected from a group consisting of CloneZyme Glycosidase Gly001-002, Gy001-003, Gly001-004 and Gly001-008.

In especially preferred embodiments of the present invention, there is provided a process for the preparation of long-chain alkyl glycosides, comprising reacting at least one substrate selected from a group consisting of carbohydrates and carbohydrate sources and at least one fatty alkanol of at least eight carbon atoms in a medium consisting of at least one enzyme as hereinbefore defined and a reaction promoter selected from the group consisting of a $C_1$–$C_4$ alcohol, SDS, a long-chain alkyl glycoside, dioxane, acetone, dimethylsulfoxide, and sulfobutanedioic acid 1,4-bis (2-ethylhexyl) ester sodium salt and mixtures thereof at a pH of about 3.5–7.0 wherein said reaction promoter constitutes less than 50% by weight of the reactive mixture.

In especially preferred embodiments of the invention, said reaction promoter constitutes less than 30% by weight of the reactive mixture.

In other preferred embodiments of the present invention said reaction promoter is selected from the group consisting of formamide, methyl formamide and dimethyl formamide.

Hildebrand and Scott designated the energy of vaporization per $Cm^2$ as the cohesive energy density and its square root as the solubility parameter. It is assumed that the cohesive energy, E, arises from contributions from hydrogen bonding $E_H$, as well as permanent-dipole- permanent-dipole interactions, $E_P$ and nonpolar interaction, $E_D$. The square roots of $E_H$, $E_P$ and $E_D$ per $Cm^2$ are the hydrogen bonding, polar and dispersion components of the solubility parameter. It was found that the first two are sufficient for selecting a suitable promoter for the reaction. Solubility parameter components for various compounds could be found in many sources including Kirk Othmer's Encyclopedia of Chemical Technology.

It was found that the most suitable promoters for the reaction in the present invention have a polar component of solubility parameter in the range of 5–13 and a hydrogen bonding component of solubility parameter in the range of 4–11.

In another aspect of the present invention, there is provided a process for the preparation of long-chain alkyl glycosides, comprising reacting a glucose-containing reactant obtained from starch hydrolysis and a $C_8$ to $C_{18}$ fatty alcohol in the presence of an enzyme as hereinbefore defined and a reaction promoter selected from the group consisting of methanol, ethanol, and isopropanol and mixtures thereof, at a pH of about 3.5–7.0 wherein said reaction promoter constitutes less than 50% by weight of the reactive mixture; said process further comprising the steps of separating the resulting aqueous and organic phases, and removing said reaction promoter from said organic phase, whereupon said remaining organic phase separates into a first phase containing excess reagent and a second phase containing the long-chain alkyl glycoside product.

The thermally stable enzymes used in the process of the present invention may be dissolved or immobilized, and thus said enzymes can be present in either of the above forms during the reaction.

It is known that alcohol solubility in water decreases with increasing alkyl chain length (propanol is fully miscible, butanol—7.8%, hexanol—0.58%, octanol—0.06% and decanol <0.01%). Low solubility might be one explanation for decrease in synthesis yield with augmentation of chain length. Increasing fatty alcohol concentration next to the enzyme can be achieved through application of a cosolvent, a compound that dissolves both the aqueous solution of the glucose containing the reagent and the fatty alcohol. G. Vic, et al. [*Tetrahedron Letters,* Vol. 33, pp. 4567–4570 (1992)] have tested the enzymatic reaction of glucose and alcohols with up to 8 carbon atoms. The co-solvent in the single phase system was acetonitrile and its content in the system was 9 times the content of all other components. Such high proportions of co-solvent increase the volume to be handled and thereby the capital cost. In addition, it dilutes the product and increases the operation costs for product separation and concentration.

Thus, it will be realized that there is no simple explanation, and it is also not readily evident, how the system of the present invention succeeds in the preparation of long-chain alkyl glycosides when the prior art failed to do so.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Fractions of mg of some of the Glysosidase CloneZyme thermal stable glycosidases, in free form, were tested in reaction media consisting 700 mg dodecanol as the long chain alkanol, 50 mg of beta methyl glycoside as the substrate, 160 mg formamide as reaction promoter and 40 mg of 0.1M phosphate buffer.

The reaction medium was shaken strongly, while at 80° C. for 2 hours and then analysed. The rates of dodecylglycoside formation in terms of micromole per day per mg of enzyme were: Gly001-02=644, Gly001-03=263 and Gly001-08=186.

These rates are more than three orders of magnitude smaller than those reported by RBI for the reaction it tested. They are, however, much higher than the highest figures reported so far for other enzymes.

In a comparative test Sigma's beta—glycosidase (1.5 mg of it in free form) was tested in reaction media consisting 720 mg dodecanol as the long chain alkanol, 72 mg of beta-methyl glycosidase as the substrate, 230 mg formamide as reaction romoter and 41 mg of 0.1 M phosphate buffer. The reaction rate was 12 micromole per day per mg of enzyme.

EXAMPLE 2

Dodecyl glucoside formation in a single-liquid-phase medium was tested with no addition of water.

About 30 mg of Dowex 50-X, carrying about 0.05 mg immobilized enzyme were added to 750 mg dodecanol and 50 mg of methyl beta glycoside at 80° C. At that temperature most of the substrate did not dissolve. Strong shaking was applied for 30 hours. The reaction could be followed by the gradual disappearance of the methyglycoside crystals and the formation of a second liquid phase, heavier than the main reaction medium. The reaction rate found for Gly001-02 and for Gly001-08 were about 30 and about 65 micromole per day per mg of enzyme respectively.

These results show that the tested enzymes were highly active without the addition of water to the reaction medium. Low water content is highly beneficial for alkyl glycoside formation. Nothing in the information provided by RBI teaches this high activity in such low water activity conditions. Beta glycosidase from almonds, which previous to the present invention was though to be the most efficient enzyme, is deactivated at low water activities.

Note that, in the condition selected for the present example, Gly001-08 was more active than Gly001-02, contrary to the data supplied by RBI and to what was found in the conditions of Example 1.

EXAMPLE 3

About 30 mg of Dowex 50-X, carrying about 0.05 mg immobilized Gly001-08 were added to a reaction medium containing 100 mg glucose as the substrate, 500 mg dodecanol, 6.1 mg methanol, and 6.1 mg of 0.1M phosphate buffer. The reaction medium was strongly shaken at 80° C. After 21 hours the reaction rate was about 6.5 micromole per day per mg of enzyme, indicating a significantly slower rate for glucose as substrate (as know also for reactions of other enzymes).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the preparation of long-chain alkyl glycosides, comprising reacting at least one substrate selected from a group consisting of carbohydrates and carbohydrate sources and at least one fatty alkanol of at least eight carbon atoms in a medium comprising at least one glycosidase enzyme having a temperature optimum greater than 60° C. and having thermal stability half-life of greater than 24 hours at 80° C., wherein said enzyme is characterised by the ability of 0.05 mg of said enzyme to catalyze a reaction between 750 mg dodecanol and 50 mg of beta methyl glycoside at 80° C. to achieve a rate of dodecyl glycoside formation of at least 20 micromole per day per mg of the enzyme.

2. A process for the preparation of long-chain alkyl glycosides according to claim 1, wherein said enzyme is characterised by the ability of 0.05 mg of said enzyme to catalyze a reaction between 750 mg dodecanol and 50 mg of beta methyl glycoside at 80° C. to achieve a rate of dodecyl glycoside formation of at least 50 micromole per day per mg of the enzyme.

3. A process for the preparation of long-chain alkyl glycosides according to claim 1, wherein said enzyme is characterised by the ability of 0.05 mg of said enzyme to catalyze a reaction between 750 mg dodecanol and 50 mg of beta methyl glycoside at 80° C. to achieve a rate of dodecyl glycoside formation of at least 100 micromole per day per mg of the enzyme.

4. A process according to claim 1, wherein said carbohydrates are selected from a group consisting of mono-, di-, and tri-sugars.

5. A process according to claim 1, wherein said carbohydrates sources are selected from a group consisting of glycosides made of mono-, di-, and tri-sugars and C1 to C4 alkanols.

6. A process according to claim 1, wherein said enzyme is selected from the CloneZyme Glycosidase Library of Recombinant BioCatalysis Inc. (RBI).

7. A process according to claim 6, wherein said enzyme is selected from a group consisting of CloneZyme Glycosidase Gly001-002, Gy001-003, Gly001-004 and Gly001-008.

8. A process according to claim 1, wherein said reaction is effected at a temperature higher than 50° C.

9. A process according to claim 1, wherein said reaction is effected at a temperature higher than 70° C.

10. A process according to claim 1, wherein said medium consists of at least two liquid phases, one of which has a substrate to alkanol weight ratio of at least 2:1 and the other has a substrate to alkanol weight ratio of at least 1:2.

11. A process according to claim 1, wherein said medium contains a reaction promoter effective to promote the formation of said alkyl glycoside.

12. A process according to claim 11, wherein said reaction promoter is present in an amount of less than about 50 wt % of the total medium.

13. A process according to claim 11, wherein said reaction promoter dissolves at least 10 weight units of said substrate per 100 weight units of said reaction promoter.

14. A process according to claim 11, wherein said reaction promoter dissolves at least 20 weight units of said alkanol per 100 weight units of said reaction promoter.

15. A process according to claim 1, wherein the water content of said medium is less than 6%.

16. A process according to claim 1, wherein the water content of said medium is less than 3%.

17. A process according to claim 1, wherein the pH in said medium is kept between 3 and 8.

18. A process according to claim 10, wherein the pH in said liquid phase having a substrate to alkanol weight ratio of at least 2:1 is kept between 3 and 8.

19. A process according to claim 1, wherein said substrate is obtained through starch hydrolysis.

20. A process according to claim 11, wherein said reaction promoter is selected from the group consisting of solvents having a polar component of solubility parameter in the range 5–13, and a hydrogen bonding component of solubility parameter in the range of 4–11.

21. A process for the preparation of long-chain alkyl glycosides, comprising:

reacting at least one substrate selected from a group consisting of carbohydrates and carbohydrate sources and at least one fatty alkanol of at least eight carbon atoms in a medium comprising at least one glycosidase enzyme having a temperature optimum greater than 60° C. and having thermal stability half-life of greater than 24 hours at 80° C., wherein said enzyme is characterised by the ability of 0.05 mg of said enzyme to catalyze a reaction between 750 mg dodecanol and 50 mg of beta methyl glycoside at 80° C. to achieve a rate of dodecyl glycoside formation of at least 20 micromole per day per mg of the enzyme, and a reaction promoter selected from the group consisting of methanol, ethanol, and isopropanol and mixtures thereof, at a pH of about 3.5–7.0 and wherein said reaction promoter constitutes less than 50% by weight of the reactive mixture;

said process further comprising the steps of separating the resulting aqueous and organic phases, and removing said reaction promoter from said organic phase, whereupon said remaining organic phase separates into a first phase containing excess reagent and a second phase containing the long-chain alkyl glycoside product.

* * * * *

UNITED STATES PATENT AND TRADEMARK OFFICE
CERTIFICATE OF CORRECTION

PATENT NO. : 6,274,349 B1
DATED : August 14, 2001
INVENTOR(S) : Aharon Meir Eyal, Asher Vitner and Tal Reuveni It is certified that error appears in the above-identified patent and that said Letters Patent is hereby corrected as shown below:

<u>Column 9,</u>
Lines 61-62, delete "carbohydrates" and insert -- carbohydrate --.

<u>Column 10,</u>
Line 17, insert -- reaction -- between "total" and "medium".

Signed and Sealed this

Eleventh Day of June, 2002

*Attest:*

*Attesting Officer*

JAMES E. ROGAN
*Director of the United States Patent and Trademark Office*